United States Patent [19]

Tarello et al.

[11] Patent Number: 4,747,839
[45] Date of Patent: May 31, 1988

[54] DISPOSABLE HYPODERMIC SYRINGE WITH PLASTIC SNAP-ON NEEDLE HUB AND HEAT SHRINK SEAL THEREFOR

[75] Inventors: William R. Tarello, Bethesda; Claudio Lopez, Darnestown, both of Md.

[73] Assignee: Survival Technology, Inc., Bethesda, Md.

[21] Appl. No.: 942,727

[22] Filed: Dec. 17, 1986

[51] Int. Cl.$^4$ ............................................. A61M 5/325
[52] U.S. Cl. ............................ 604/240; 128/DIG. 18
[58] Field of Search ............... 604/111, 89, 201, 240, 604/202; 128/DIG. 18

[56] References Cited

U.S. PATENT DOCUMENTS

| | | | |
|---|---|---|---|
| 3,387,609 | 6/1968 | Shields | 604/202 |
| 3,413,974 | 12/1968 | Cohen | 604/201 |
| 3,437,090 | 4/1969 | Sarnoff | 604/202 |
| 4,475,903 | 10/1984 | Steenhuisen et al. | 604/111 |
| 4,568,336 | 2/1986 | Cooper | 604/240 |
| 4,624,393 | 11/1986 | Lopez | 604/240 X |

*Primary Examiner*—John D. Yasko
*Attorney, Agent, or Firm*—Witherspoon & Hargest

[57] ABSTRACT

A disposable hypodermic syringe having a cylindrical barrel open at both its forward and rearward ends, with the forward tooled end having a necked down portion terminating in an annular flange having an outer diameter greater than that of the necked down portion and less than that of the cylindrical barrel, a stopper positioned in the necked down portion of the cylindrical barrel to seal off the tooled end of the barrel, a resilient plastic needle hub assembly fitted on the forward end of the cylindrical barrel. The hub assembly including a cylindrical body having both a forward and a rearward end, a nose portion extending forwardly from the forward end of the cylindrical body, a needle affixed to the nose portion away from the forward end of the cylindrical body, the cylindrical body being sized whereby it will resiliently fit over and engage the annular flange of the necked down portion of the cylindrical barrel to operatively retain the needle hub assembly on the cylindrical barrel with a sleeve of heat shrinkable plastic fitted over a portion of the hub assembly and contiguous cylindrical barrel whereby when heat is applied the sleeve will shrink to firmly engage the aforedescribed syringe portions and thereby provide an air tight seal between the hub body and the cylindrical barrel and in addition whereby the shrink tension will cause the hub body to more firmly engage the annular flange.

4 Claims, 2 Drawing Sheets

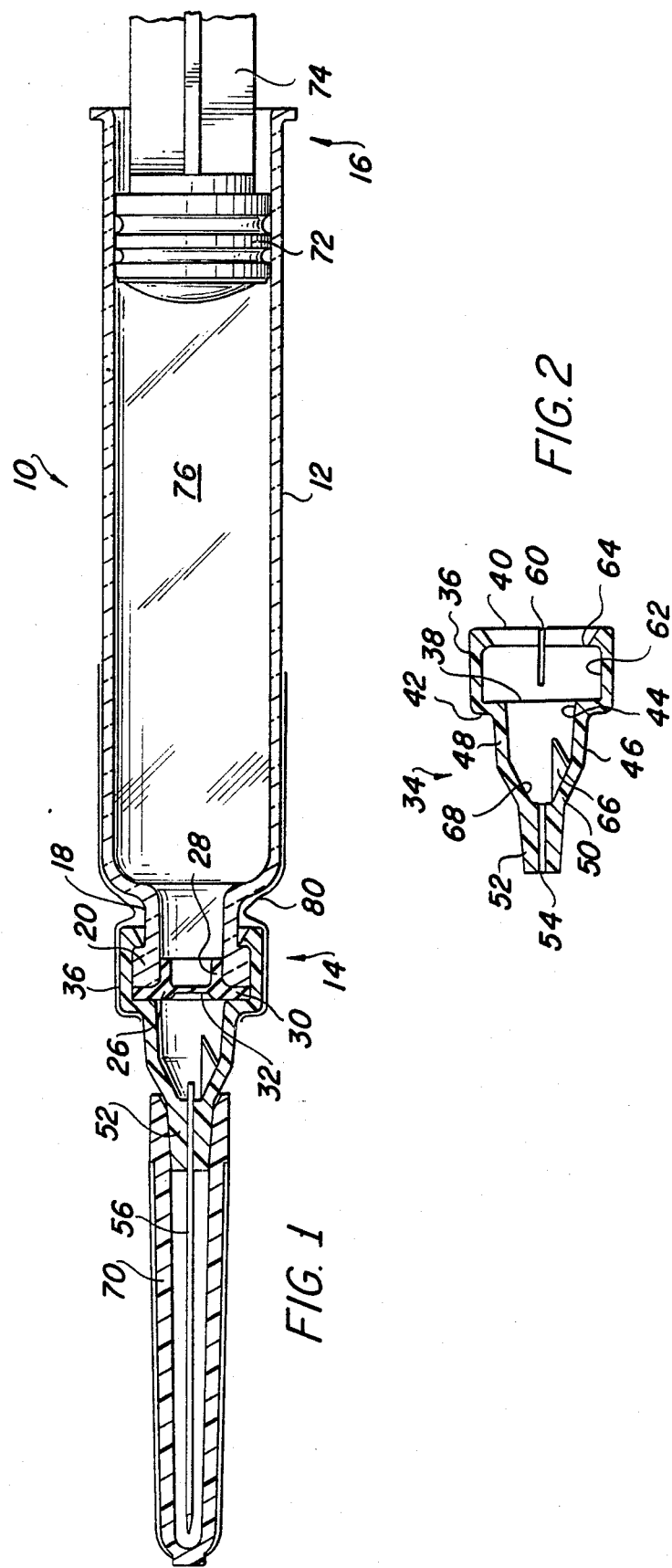

DISPOSABLE HYPODERMIC SYRINGE WITH PLASTIC SNAP-ON NEEDLE HUB AND HEAT SHRINK SEAL THEREFOR

This invention relates to disposable hypodermic syringes and more particularly to such syringes which are provided with plastic snap-on needle hubs and heat shrink seals therefor.

BACKGROUND AND OBJECTS

Basically, the disposable hypodermic syringe embodied in this invention comprises a cylindrical glass cartridge barrel which is open at both its forward and its rearward ends. The forward end has a necked down portion terminating in an annular flange having an outer diameter greater than that of the necked down portion and generally less than that of the cylindrical barrel. A stopper closes off the opening in the forward end of the cylindrical barrel formed by the annular flange.

A plastic needle hub is fitted onto the necked down end of the cylindrical barrel. The plastic hub comprises a cylindrical body having a forward end mounting a needle. The diameter of the inner surface of the hub cylindrical body is sized to fit snugly over the annular flange of the cylindrical barrel and terminates in an inwardly directed annular locking lip having an inner diameter less than the outer diameter of the annular flange of the cylindrical barrel and adapted to snugly engage the backside of the annular flange after the hub cylindrical body is snapped onto and over the annular flange. It should be noted that the plastic hub is made from a material which will give slightly and thus provide the snap-on qualities desired in the hub.

The rearward portion of the cylindrical barrel is provided with a sealing piston to thereby provide a sealed chamber between the stopper in the forward end and the piston in the rearward end. Suitable operating means are associated with the piston to assist in the injection procedure.

The industry for a number of reasons has been leaning toward the use of plastic hubs particularly for use in disposable units. As might be expected plastic has brought new problems into the field. First of all, the sterilization problem appears. How much heat can the plastic stand and just what kind of heat may it be. Secondly, how do you attach the needle to the plastic hub and thirdly, how do you attach the hub to the cartridge tube or body.

In this particular plastic hub the material used is polycarbonate. It will withstand the requisite heating for sterilization purposes and the needle may be secured thereto using UV curable adhesives. It is capable of slight giving i.e., elastic enough to allow and provide the desired snap-on quality for the hub body onto the annular flange on the cylindrical barrel.

The use of plastic for making cannula hubs is well known in the prior art. For example, Keller U.S. Pat. No. 3,372,697 discloses plastic hubs wherein the materials may be either polypropylene or polycarbonate. In a more recent development, U.S. Pat. No. 4,240,423 to Akhaui discloses a transparent polycarbonate material wherein the deflection temperature is no lower than 270° F. and is therefore suitable for use where autoclave temperature may range from 240° to 260° F. It is further stated that the cannula may be secured to the hub by an expoxy-type adhesive that will withstand steam sterilization temperatures of 240° to 260° F.

With regard to the securing of plastic hubs to the cartridge tube the patent to Keller U.S. Pat. No. 3,372,697 is again very interesting. In FIG. 8 the hub skirt 76 is deformed at 82 by a spinning operation to secure the hub to the enlarged head of the cartridge. It should be noted that the inner end of the cannula 80 extends inwardly beyond the stopper 75 so that the medicament will never come in contact with the cannula hub. In the embodiment illustrated in FIG. 5 a snap-on arrangement is provided wherein flange 62 of the hub body 60 overlys the rear face of cartridge head 52. Here it must be observed that the body 60 is directly bonded to the cartridge head 52 by means of bonding material 56. Again the medicament cannot come in contact with the hub at anytime.

Yet another way of securing a needle hub to the cartridge tube is illustrated in FIG. 1 of Sarnoff U.S. Pat. No. 3,421,155 wherein needle holder 20 is clamped to the vial by spinning an aluminum collar 28 over the shoulder of a terminal portion 30 of the vial and over an annular flange 32 integral with the holder.

The use of shrinkable plastic material as a sealing means is well known in the prior art for specific purposes. For example, Steenhuisen et al U.S. Pat. No. 4,475,903 is directed to a disposable syringe comprising a barrel which has on its tooled end a needle connection with an injection needle and needle guard. A sealing member is provided for the needle guard and consists of a sleeve of shrinkable plastic material. This sleeve is shrunk on one side around the needle connection and/or around the barrel or a front part of the barrel and, on the other side around a part of the needle guard adjoining the needle connection. See FIG. 2 of the drawings for such an arrangement. It should be noted that the wrap is provided with perforations 19 to make it easier to remove the needle guard by breaking the seal at the weakened area. See FIG. 3. It is stated in the specification that although an unperforated sleeve can contribute to maintenance of the sterility of the syringe, the perforated embodiment is preferred. It should be further noted, as shown in FIG. 4, the shrink wrap may extend over the entire syringe including the barrel. Apparently having the wrap around the barrel protects the barrel from some type of breakage.

With the foregoing in mind it is an object of this invention to provide a disposable hypodermic syringe having a cylindrical glass barrel open at both its front and rearward ends with the forward tooled end terminating in an annular flange, a stopper closing the tooled end of the barrel, and a plastic needle hub having a cylindrical body adapted to snugly fit over the annular flange and with a tightly engaging wrap firmly engaging both the hub body and the adjacent portion of the glass barrel to provide a two-fold function namely to enhance the seal formed between the hub body and the annular flange and to assit in retaining the hub body firmly on the annular flange.

It is another object of this invention to make the wrap set forth in the preceding object with a heat shrinkable material.

It is yet another object of this invention to provide the hub body with several slits to increase the resiliency of the body to aid in assembly onto the annular flange.

The foregoing and additional objects and advantages will become more apparent when taken in conjunction with the following detailed description and drawings covering a preferred embodiment of this invention.

IN THE DRAWINGS

FIG. 1 is a cross sectional view of the entire syringe assembly including the needle guard, FIG. 2 is a sectional view of the snap-on needle hub; and FIG. 3 is a partial exploded view illustrating the basic components in alignment for assembly.

DETAILED DESCRIPTION

Figure 3:
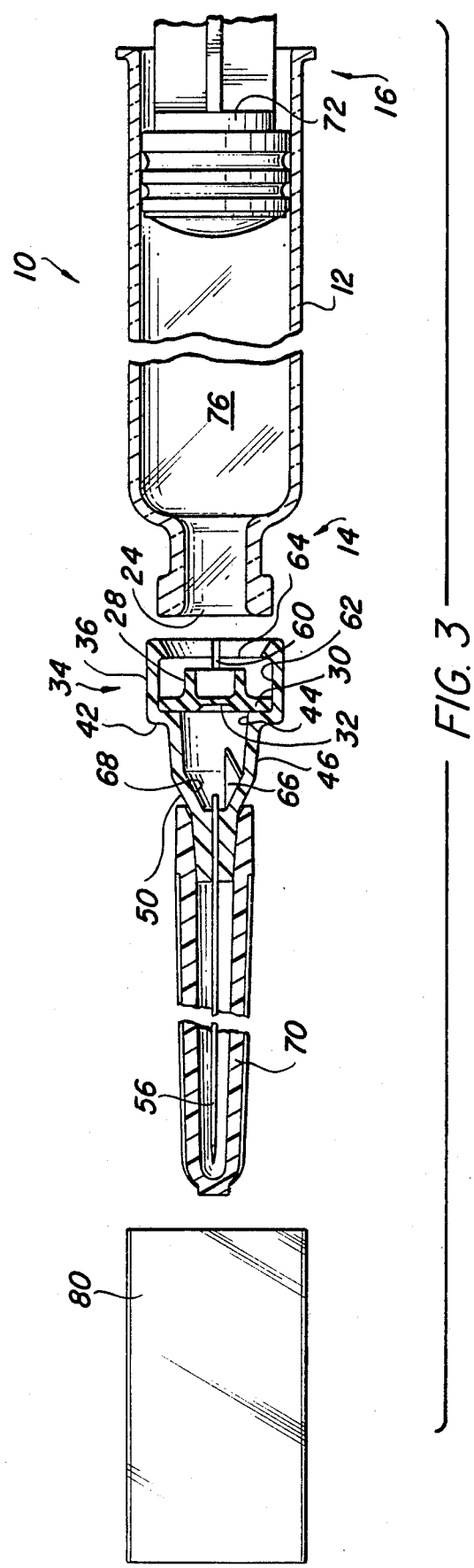

As illustrated in the various drawings the disposable hypodermic syringe 10 of this invention comprises a cylindrical glass barrel 12 which is open at both its forward and rearward ends 14 and 16 respectively. The forward tooled end has a necked-down portion 18 terminating in an enlarged annular flange 20 having its outer diameter greater than that of the necked down 18 and less than that of the cylindrical barrel 12. The diameter of the opening 24 in the annular flange 20 is equal to that in the necked down portion 18 and less than that of cylindrical barrel 12.

A stopper 26 is positioned in the forward end of the cylindrical barrel 12 to close off the opening in that end. The stopper 26 comprises a cylindrical plug portion 28 fitting into the opening formed by the inside diameter of the annular flange 20 and the necked down portion of the cylindrical barrel 12. The cylindrical plug portion 28 of the stopper 26 is closed off by a flat disc like cap 30 having a diameter generally equal to the outer diameter of the annular flange 20 and resting thereon as shown in FIG. 1. The forward end 14 of the cylindrical barrel 12 is thus closed by stopper 26. The center portion 32 of the stopper 26 is provided with an area of reduced thickness to assist in the bursting of the stopper when the syringe is activated.

A plastic needle hub 34 is resiliently fitted onto the annular flange 20 of the cylindrical barrel 12 as illustrated in FIG. 1. More specifically, as shown in FIG. 2, the plastic hub 34 comprises a cylindrical body 36 having both a forward and a rearward open end repectively 38 and 40. The forward end of the hub body 36 terminates in an inwardly directed annular shoulder 42 which extends generally perpendicular to the cylindrical body 36 of the hub 34. The inner edge 44 of the annular shoulder 42 forms a circle having a diameter generally equal to or slightly greater than the inner diameter of the annular flange 20 on the forward end of the glass barrel 12. The cap portion 30 of the stopper 26 is held between the hub's inwardly directed shoulder 42 and the confronting face of the annular flange 20 on the glass barrel 12.

A nose portion 46 extends forwardly from the inward portion of the hub annular should 42. More particularly, a first portion 48 of the nost portion 46 has slightly conical shape with its larger end connected to the inward portion of the hub annular shoulder 42. The smaller end connects with an inwardly and forwardly directed second conical portion 50 which in turn connects with a third portion 52 having a slight taper directed inwardly and forwardly. The third portion 52 has a centrally disposed hub 54 sized to receive a needle 56.

The cylindrical body 36 of the hub 34 is provided with four slits 60 equi-spaced therearound. In addition, the inner surface 62 of the body 36 is provided with an inwardly directed locking lip 64 adapted to fit in behind the annular flange 20 to retain the hub and stopper assembled to the cylindrical barrel 12. More particularly, the hub is made of a somewhat resilient plastic such as polycarbonate and has an inner surface 62 sized to resiliently pass over the annular flange 20 whereby the locking lip 64 will engage the rearward edge of the annular flange 20 to retain the hub in assembled postion as illustrated in FIG. 1.

As best shown in FIG. 2 a spike 66 extends rearwardly from the inner surface 68 of the second portion 50 of the nose body 34 with its sharp end pointing toward the thinned portion 32 of the stopper 26. A suitable needle guard 70 is positioned over the needle 56 and is affixed to the third portion 54 of the nose body 34.

As shown in FIGS. 1 and 3 the rearward open end of the cylindrical barrel 12 is closed off by a slidable piston 72 which may be connected to an operating member 74. The space between the stopper 26 and the piston 72 forms the medicament chamber 76.

For assembling of the syringe reference is made to FIG. 3. First, the piston 72 is positioned in the cylindrical barrel 12 then with the barrel 12 in a vertical position the medicament is introduced into the medicament chamber 76, next the hub assembly with needle guard in place is assembled to the glass barrel 12 by passing the split hub body 36 down over the annular flange 20 so that the locking lip 64 will engage the rearward edge of said annular flange 20 as shown in FIG. 1 to securely retain the hub assembly on the glass barrel 12. Next, heat shrinkable plastic sleeve 80 is slipped down over the hub assembly and positioned longitudinally so that there is a slight over hang on the forward end of the hub body 34 while the other end extends down over a portion of the glass barrel 12. After this heat is applied to cause the sleeve 80 to shrink and firmly engage the areas it encompasses so as to form an air tight seal between the hub body portion 34 and the glass barrel 12. In addition, the shrink sleeve 80 serves to assist in retaining the split hub 34 assembled to the end of the glass barrel 12. With this type of seal it will be readily apparent if the hub body 36 is broken away from the glass barrel 12.

What is claimed is:

1. A disposable hypodermic syringe comprising a cylindrical barrel open at both its forward and rearward ends, the forward tooled end having a necked down portion terminating in an annular flange having an outer diameter greater than that of the necked down portion and less than that of the cylindrical barrel, a stopper positioned in the necked down portion of the cylindrical barrel to seal off the forward end of the said barrel, a unitary resilient plastic needle hub assembly fitted on the forward end of the cylindrical barrel, said hub assembly comprising a cylindrical body having both a forward and a rearward end, a nose portion extending forwardly from the forward end of the cylindrical body, a needle affixed to the nose portion away from the forward end of the cylindrical body, said cylindrical body being sized whereby it will resiliently fit over and engage the annular flange of the necked down portion of the cylindrical barrel to operatively retain the needle hub assembly on the cylindrical barrel, said hub body being provided with internal locking means engaging behind the annular flange to assist in retaining the hub assembly on the cylindrical barrel, a sleeve of heat shrinkable plastic fitted over a portion of the hub assembly and contiguous cylindrical barrel whereby when heat is applied the sleeve will shrink to firmly engage the aforedescribed syringe portions and thereby provide an air tight seal between the hub body and the cylindrical barrel and in addition whereby the shrink tension will cause the hub body to more firmly engage the annular flange.

2. The invention as set forth in claim 1 and wherein the hub body internal locking means comprises an internal annular locking lip fitting behind the annular flange.

3. The invention as set forth in claim 2 and wherein the hub body is provided with at least one slit to add resiliency and ease of assembly over the annular flange.

4. The invention as set forth in claim 3 and wherein the sleeve of heat shrinkable plastic is fitted over and overlaps the entire body portion of the hub assembly and extends rearwardly onto the cylindrical barrel whereby when heat is applied the sleeve will shrink and firmly engage the hub body and down closely adjacent the necked down portion of the tooled portion of the cylindrical barrel and firmly against the cylindrical barrel covered thereby, so that there is an air tight seal provided between the hub body and the annular flange of the cylindrical barrel and whereby the tension produced in the sleeve when shrunk will cause the hub body to more firmly engage the annular flange.

* * * * *